United States Patent
Von Busch et al.

(10) Patent No.: US 10,521,563 B2
(45) Date of Patent: Dec. 31, 2019

(54) MULTI-TREATMENT PLANNING APPARATUS AND METHOD

(71) Applicant: KONINKLIJKE PHILIPS ELECTRONICS N.V., Eindhoven (NL)

(72) Inventors: Heinrich Von Busch, Aachen (DE);
Jens-Christoph Georgi, Aachen (DE);
Bernd Schweizer, Herzogenrath (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 825 days.

(21) Appl. No.: 14/153,373

(22) Filed: Jan. 13, 2014

(65) Prior Publication Data

US 2014/0142911 A1    May 22, 2014

Related U.S. Application Data

(62) Division of application No. 12/675,974, filed as application No. PCT/IB2008/053429 on Aug. 26, 2008, now Pat. No. 8,660,800.

(60) Provisional application No. 60/969,708, filed on Sep. 4, 2007.

(51) Int. Cl.
G06F 19/00     (2018.01)
G16H 50/50     (2018.01)

(52) U.S. Cl.
CPC ...... G06F 19/3481 (2013.01); G06F 19/3456 (2013.01); G16H 50/50 (2018.01)

(58) Field of Classification Search
CPC .................................................. G06F 19/3481
USPC .......................................................... 702/19
See application file for complete search history.

(56) References Cited

U.S. PATENT DOCUMENTS

| | | | |
|---|---|---|---|
| 4,048,064 | A | 9/1977 | Clark, III |
| 6,127,311 | A | 10/2000 | Davankov et al. |
| 6,238,795 | B1 | 5/2001 | Strom et al. |
| 6,735,277 | B2 | 5/2004 | McNutt et al. |
| 2002/0095259 | A1 | 7/2002 | Agur et al. |
| 2003/0144798 | A1 | 7/2003 | Gardner |
| 2003/0152502 | A1 | 8/2003 | Lewis et al. |
| 2004/0254736 | A1 | 12/2004 | Michelson et al. |

FOREIGN PATENT DOCUMENTS

| | | |
|---|---|---|
| EP | 0945815 A2 | 9/1999 |
| WO | 2006136449 A1 | 12/2006 |
| WO | 2007001915 A2 | 1/2007 |
| WO | 2007042851 A1 | 4/2007 |

OTHER PUBLICATIONS

Martin, et al., Synergistic antitumour effect of a combination of toremifene and interferon-a on ZR-75-1 human breast cancer cells: Dependence on interferon-a subtype, Oncology Reports, 2002, pp. 379-382, vol. 9.
Reynolds, et al., Evaluating Response to Antineoplastic Drug Combinations in Tissue Culture Models, Methods in Molecular Medicine, 2005, pp. 173-183, vol. 110.
Pierce Biotechnology, Hydrazide Beads Instructions, 2006, pp. 1-3, No. 20202, www.piercenet.com.
Biosoft, CalcuSyn Dose-Effect Analyzer for Single and Multiple Drugs, downloaded Aug. 28, 2008, 2 sheets, http://www.biosoft.com/w/calcusyn.htm.
Pierce Biotechnology, home page, downloaded Aug. 30, 2007, 1 sheet, http://www.piercenet.com.
Pierce Biotechnology, Polystrene Hydrazide Beads product page, downloaded Aug. 30, 2007, 1 sheet, http://www.piercenet.com/products/browse.cfm?fldID=02050502.

*Primary Examiner* — Jerry Lin

(57) ABSTRACT

A treatment planning apparatus includes a treatment modeler. The treatment modeler uses models of a plurality of treatment modalities in a treatment space to generate a treatment protocol that includes one or more the modalities in the treatment space. In one implementation, a treatment modality includes the removal of targeted treatment agents from an object.

20 Claims, 4 Drawing Sheets

Figure 1:
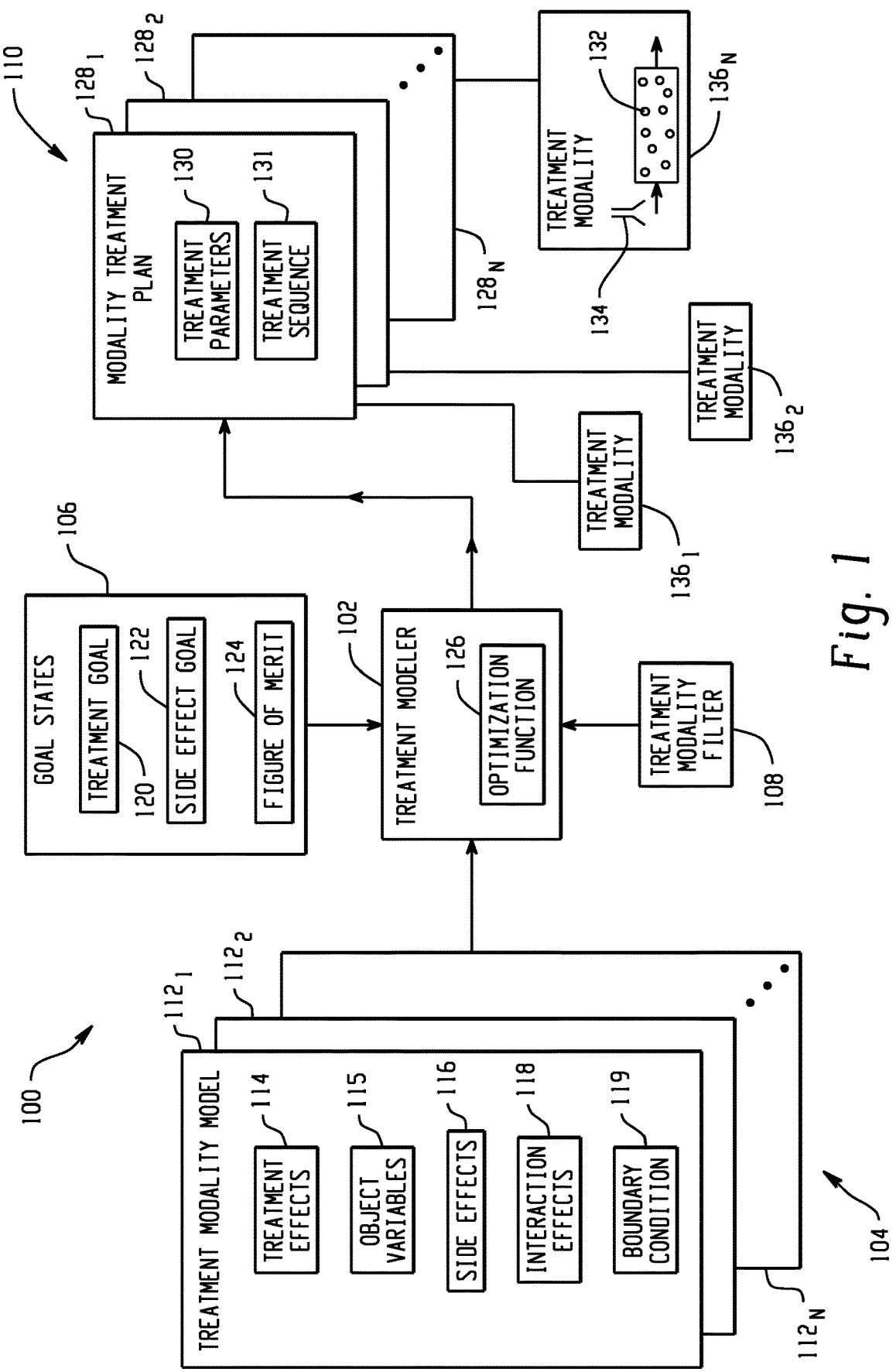

MULTI-TREATMENT PLANNING
APPARATUS AND METHOD

CROSS REFERENCE TO RELATED
APPLICATIONS

This application is a divisional of patent application Ser. No. 12/675,974 filed Mar. 2, 2010 which was a national filing of PCT application Ser. No. PCT/IB2008/053429, filed Aug. 26, 2008, published as WO 2009/031073 A2 on Mar. 12, 2009, which claimed the benefit of U.S. provisional application Ser. No. 60/969,708 filed Sep. 4, 2007, all of which are incorporated herein by reference.

The present application relates to treatment planning in medical and other applications that benefit from the optimization or other evaluation of treatments using multiple treatment modalities.

Treatment approaches in various applications typically apply mechanical, chemical, thermal, electromagnetic, nuclear, or other energy to an object. In medical oncology, for example, treatment modalities have included surgery, chemotherapy, external radiotherapy (ERT), internal radiotherapy (IRT) such as brachytherapy, and radioimmunotherapy (RIT) agents such as Zevalin or Bexar that include monoclonal antibodies (mAb) having an affinity to CD20 antigens associated with certain cancer cells. Still other treatment modalities include thermal and cryo ablation, radio frequency ablation (RFA), high intensity focused ultrasound (HIFU), the use of perfusion modulation agents (PMAs) and other radiosensitizing agents, and the like. In many cases, an applied treatment will include contributions from more than one treatment modality.

In general, the goal of a treatment plan is to maximize the expected therapeutic effect on a target while minimizing side effects to non-target portions of the object. Again in the example of medicine, the treatment objective is ordinarily to destroy or otherwise constrain the growth of a tumor or other pathology while minimizing the damage to risk organs or otherwise healthy tissues. In oncology, this concept has been described in terms of tumor control probability (TCP) and normal tissue complication probability (NTCP) functions, which have been expressed in relation to treatment parameters such as pharmaceutical or radiation dose, dose rate, and fractionation. TCP and NTCP functions have been derived from systematic experiments in cells and animals, statistical analyses of therapeutic outcomes, and theoretical models, both for single and multiple modality treatment approaches.

Various treatment planning tools have also been developed. Again to the example of medical oncology, software-based radiation therapy planning (RTP) tools are often used to generate a treatment plan that delivers an optimal or otherwise desired spatially varying radiation dose to the patient. More specifically, RTP planning tools typically generate a treatment plan that delivers a desired, relatively high radiation dose to a tumor while minimizing the dose applied to surrounding tissues. See U.S. Pat. No. 6,735,277 to McNutt, et al., entitled Inverse Planning for Intensity Modulated Radiotherapy. Other systems and methods for recommending an optimal treatment protocol for a specific individual have also been proposed, as have systems and methods for the general patient. See U.S. Patent Publication 2002/0095258 A1 to Agur, et al., entitled System and Methods for Optimized Drug Delivery and Progression of Diseased and Normal Cells.

In a combination treatment situation, however, a second or additional treatment modality does not find the object in its original (i.e., in its untreated) state. In some cases, for example, an initial damage or sensitization to a second treatment modality is induced by the first treatment modality. Hence, optimizing each treatment in isolation is likely to produce a sub-optimal result.

Aspects of the present application address these matters and others.

In accordance with one aspect, an apparatus includes a treatment modeler that models effects of treatment modalities in a treatment space to generate a medical treatment protocol for application to a subject. The treatment modeler models an interaction between first and second treatment modalities of the treatment space.

According to another aspect, a computer readable storage medium contains instructions which, when executed by a computer, cause the computer to carry out a method. The method includes modeling a treatment effect of a first treatment modality, a side effect of the first treatment modality, and an interaction between the first treatment modality and a second treatment modality. The method also includes using a result of the modeling to generate a treatment protocol for application to an object.

According to another aspect, a method includes using a mathematical model to model a treatment effect and a side effect of first and second treatment modalities. The model includes an effect of an interaction between the first and second treatment modalities. The method also includes using a result of the modeling to generate a treatment protocol for application to an object.

According to another aspect, a filter apparatus filters a material present in a bodily fluid. The apparatus includes a carrier and an antigen carried by the carrier. The antigen has an affinity for the material present in the bodily fluid.

According to another aspect, a method includes applying a treatment agent to a patient. The treatment agent includes antibodies having an affinity to a pathology of the patient. The method also includes using a filter that includes antigens having an affinity to the antibodies to remove the agent from a bodily fluid of the patient.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
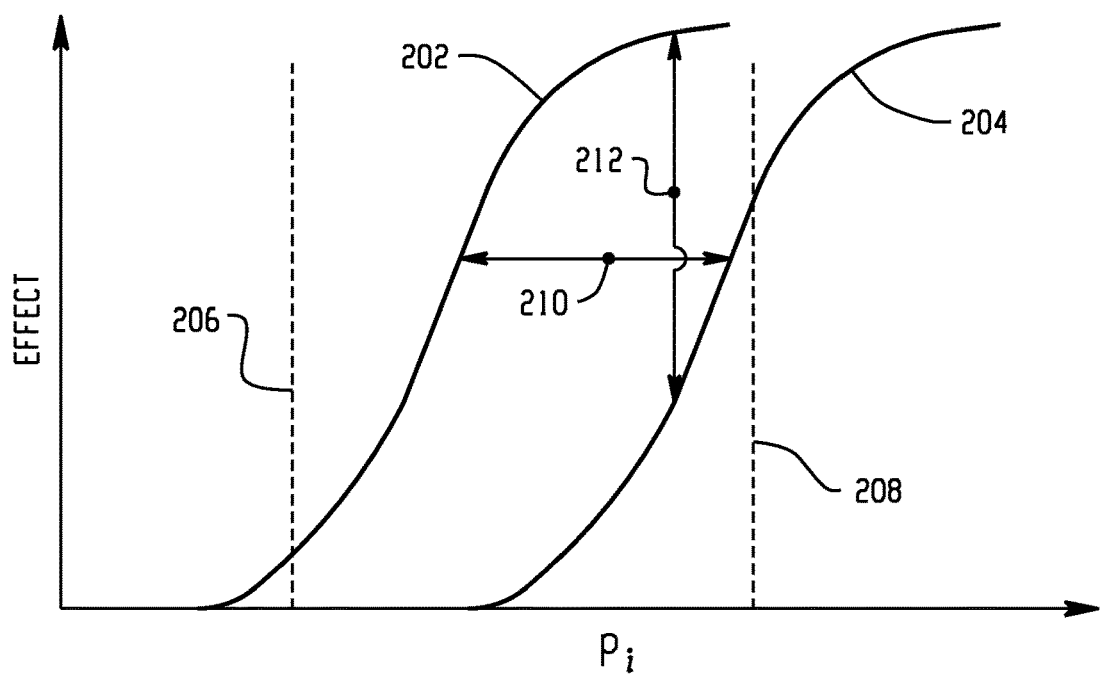
Figure 3:
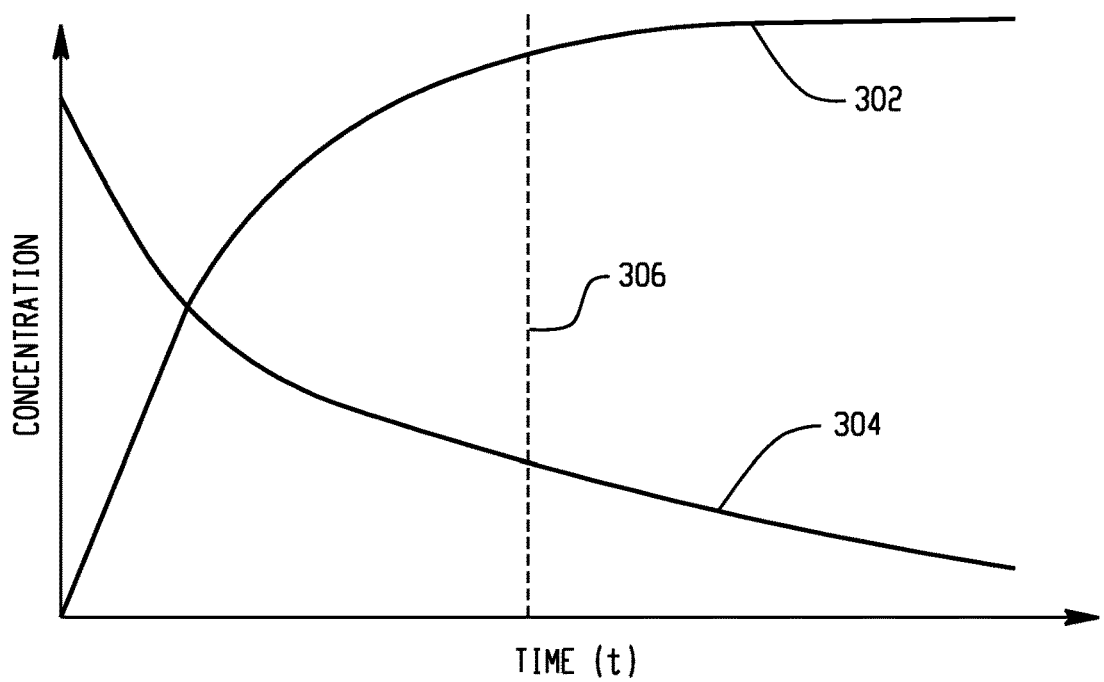
Figure 4:
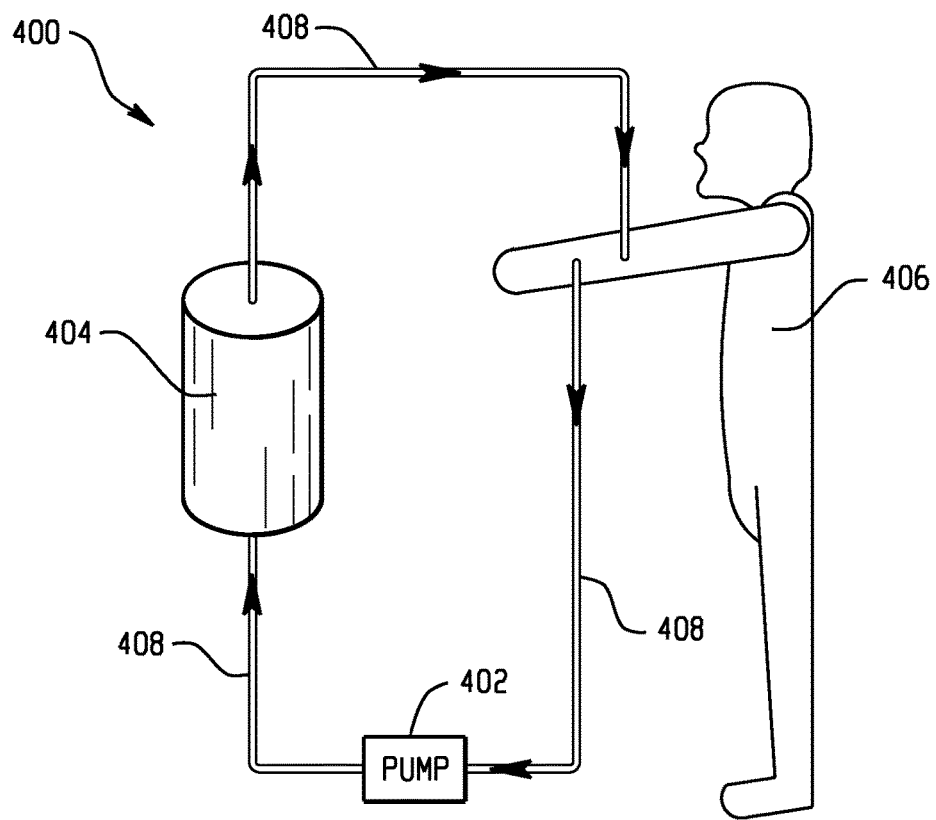
Figure 5:
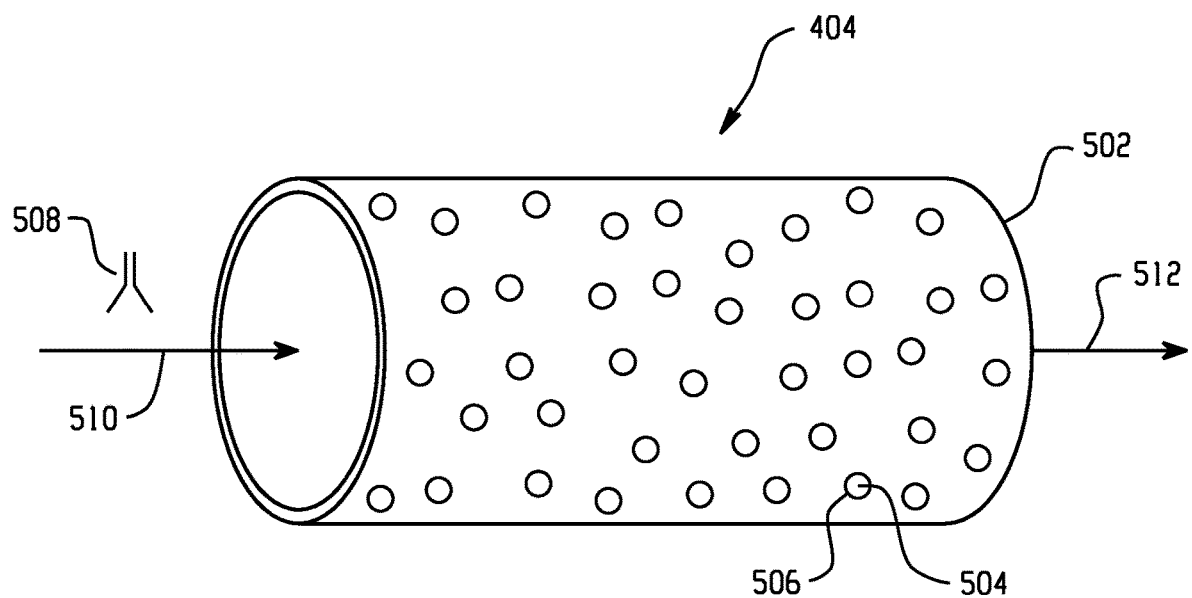
Figure 6:
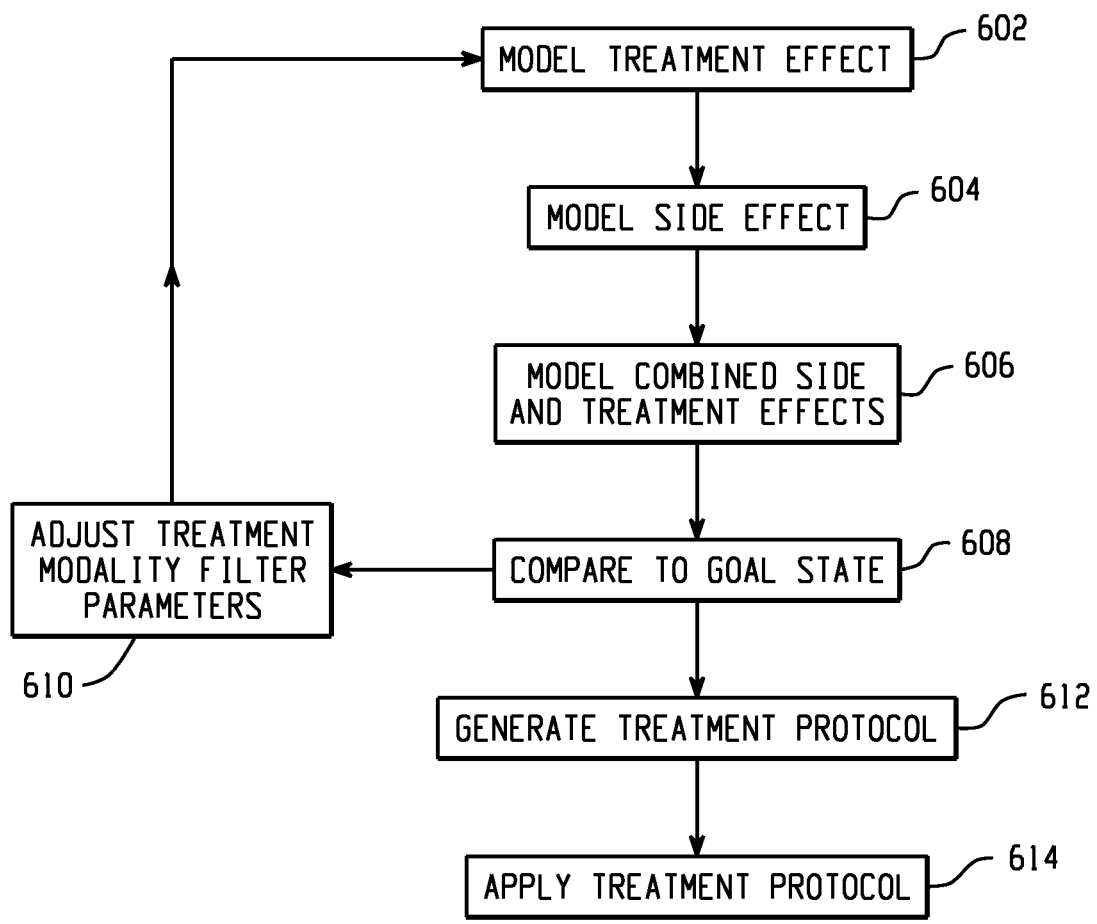

FIG. 1 depicts a treatment planning system.
FIG. 2 depicts a treatment modality model.
FIG. 3 depicts concentrations of a treatment agent.
FIG. 4 depicts a vascular filtering apparatus.
FIG. 5 depicts a filter.
FIG. 6 depicts a method.

With reference to FIG. 1, a treatment planning system 100 includes a treatment modeler 102 that uses one or more goal states 106 and information from a treatment space 104 to generate a treatment protocol 110.

The treatment space 104 includes a plurality of treatment modalities. As illustrated, treatment models $112_{1-N}$ model the treatment 114, side 116, or other effects of the various treatment modalities in the treatment space 104. Also as illustrated, the treatment models model synergistic, antagonistic, and/or other interaction effects 118 between one or more of the other treatment modalities in the treatment space 104. The effects and/or interactions of the various treatment modalities are modeled as a function of modality-specific independent variables such as one or more of an applied mechanical, chemical, or thermal, radiation, or other dose, the dose rate, fractionation, the temporal sequence and spacing of treatments applied using the treatment modalities, and the like. The treatment models 112 may also model the various effects of the treatment as a function of modality-specific object variable(s) 115 that are relevant to an object's expected response to a treatment that includes the treatment modality (or combination of modalities). The object variables 115, the values of which are ordinarily specific to the object whose treatment is being modeled, may include measurement or other information derived from various sources. Example data sources include but are not limited to qualitative or quantitative data derived from a non-destructive, medical, or other imaging examination(s) of the object, the results of chemical, electrical, mechanical, genetic, molecular diagnostic or other examination(s) of the object, information derived from examination(s) performed by humans, and demographic information such as a manufacturing date or version in the case of a manufactured object or age and gender in the case of a living object. The treatment models 112 may also include boundary condition(s) such as minimum or maximum doses, dose rates, or other boundary condition(s) relevant to a particular modality and the desired effect of this modality.

It will also be understood that the system 100 may be used in connection with adaptive treatment planning processes in which the model(s) 112 and/or the applied treatment adapts as the object reacts to one or more applied treatment(s). According to such an implementation, one or more of the treatment models 112 are implemented as adaptive treatment models that model the expected effect(s) of the treatment(s) as a function of the observed response of the object to previously applied treatment(s). The response may be evaluated with reference to the value(s) of, or changes in the value(s) of, relevant object variable(s) 115 as determined at one or more times over the course of a treatment.

The goal state(s) 106 describe one or more of the goals to be achieved via a treatment. As illustrated, the goal state(s) include one or more treatment goals 120 and side effect goals 122, it being understood the objective is ordinarily to maximize desirable treatment effects while minimizing undesirable side effects. The goal state 106 may also include a figure of merit 124 that accounts for interactions or other relationships between various goals. In the case of treatment modalities that produce different side effects 116, for example, the figure of merit 124 may reflect the relative weights assigned to those side effects. As another example, the figure of merit 124 may reflect the relative weights assigned to treatment effects 114 and side effects 116 in the case of a treatment protocol 110 that is expected to produce strong treatment effects 114 but relatively severe side effects 116 (or vice versa).

The treatment modeler 102 employs the treatment models 112, in conjunction with a suitable optimization function 126, to seek a treatment protocol 110 that optimally or otherwise satisfies the goal states 106, taking into account an interaction between treatment modalities in the treatment space 104.

As illustrated, the modeler uses a result of the modeling to generate a treatment protocol 110 that includes one or more modality treatment plans 128$_{1-N}$. The treatment plans 128 describe the treatment parameters 130 of the treatment modality or modalities to be applied. Where the treatment protocol 110 includes the use of more than one treatment modality, the protocol 110 and/or the various modality treatment plans 128 may include a treatment sequence 131 that describes the temporal sequence and/or spacing of the various treatments. In some situations, it may be desirable to use a result of the modeling to generate two (2) or more possible treatment protocols 110 (e.g., where multiple treatment protocols 110 satisfy the goal state 106, none of the treatment protocols 110 satisfy the goal state 106, two or more treatment protocols 110 are expected to produce similar results, or it is otherwise desirable to consider more than one treatment option during the course of the treatment planning process).

In one implementation, the treatment modeler 102 considers each of the N modalities in the treatment space 104 when generating the treatment protocol 110. In the general case, the treatment modeler 102 may then suggest a treatment protocol 110 that includes contributions from each of the modalities. Particularly in the case of a treatment space 104 that includes a relatively large number of treatment modalities, however, the administration of such a treatment protocol 110 may be relatively complex or otherwise impractical.

A treatment modality filter 108 may be used to filter or otherwise constrain the treatment modalities included in the treatment protocol 110. In one implementation, the filter 108 constrains the treatment modalities initially considered by the treatment modeler to a subset of the treatment space 104, for example so that only a single or other limited number of treatment modalities is considered. If the limited number of treatment modalities is unable to satisfy the goal state 106, additional or different treatment modalities may be considered by the treatment modeler 102. Viewed from another perspective, the goal state 106 may include goals such as a maximum number of treatment modalities, minimizing the number of treatment modalities, constraints or boundaries that restrict certain combinations of treatment modalities, or the like.

The number and order in which the treatment modalities are considered is ordinarily selected based on considerations such as the expected effect of a single treatment modality, quality of life and/or patient preference in the case of a human subject, availability of the treatment, cost, and the like. In one implementation, the various factors considered by the modality filter 108 are fixed. The factors may also be variable, for example in response to preferences or other information provided by a human user via a suitable user interface.

The treatment protocol 110 may also be presented to the user at one or more times during or at the conclusion of the modeling process for acceptance by or other response from the user, again via a suitable user interface. Where the modeler generates more than one treatment protocol 110, the suggested protocols 100 may be presented to the user, with the user being afforded an opportunity to respond, for example by selecting one of the suggested protocols, suggesting modifications to the protocol(s), rejecting one or more of the treatment protocols, or the like.

The relevant modality treatment plans 128 are transmitted to the corresponding treatment modalities 136$_{1-N}$ via a suitable electronic communication network, electrical interface, computer readable storage media, a human user, or the like. In one implementation, and as will be described in further detail below, a treatment modality 136 may employ ligands 132 that bind to agents or materials 134 present in an object.

The treatment modeler 102 will now be further described. FIG. 2 depicts an example treatment modality model 112 in graphical form. The abscissa or horizontal axis depicts an independent or treatment parameter $p_i$. The ordinate or y-axis, which depicts an effect of the treatment, may be expressed as a probability, an absolute value, or other appropriate fashion. A treatment effect function is illustrated by curve 202, while a side effect function is illustrated by curve 204.

In the case of radiation oncology, for example, the treatment effect function 202 may include a TCP, the side effect function 204 may include an NTCP, and the treatment parameter $p_i$ may include an applied dose. In other example, the treatment effect function 202 may include a dose applied to a target, the side effect function 204 may include a dose applied to a non-target portion of the object, and the treatment parameter $p_i$ may include one or more parameters related to the application of a spatially varying radiation or other applied energy. While only a single treatment parameter $p_i$ is depicted in FIG. 2 for clarity of illustration, it will be understood that additional treatment parameters $p_i$ (e.g., dose rate and/or application interval) may also be modeled. Boundary conditions 119 for the treatment parameter $p_i$ (e.g., minimum and maximum applied doses) are depicted at 206 and 208, respectively.

The therapeutic gap 210 between the treatment 202 and side 204 effect functions, which reflects results of the treatment at various parameter values, tends as a practical matter to limit the possible values of the treatment parameter $p_i$. The difference or Delta 212 compares the treatment effects 202 and side effects 204 at a given value of treatment parameter $p_i$ (or vector of values in the case of a multivariate model).

When a single treatment modality is considered, a goal of the treatment modeler 102 can be expressed as finding the value(s) of therapy parameter(s) $p_i$ for which:

$$\text{Delta}(p_i) = TE_1(p_i) - SE_1(p_i) \qquad \text{Equation 1}$$

reaches a maximum or other desired value, where $TE_1$ represents the treatment effect function 202 and $SE_1$ represents the side effect function 204 for the treatment modality. Where appropriate in the multivariate case, the optimization problem may also consider the interaction between the various treatment parameters $p_i$ of the treatment modality. As noted above, the optimization problem for a given treatment modality may be subject to various boundary conditions 119 and goals 106. By way of example, a given treatment modality may be limited to a given dose or dose rate, it may be necessary to ensure that the treatment effect function 202 is greater than a desired value or that the side effect function 204 is less than a desired value, or the like.

In the case of a multi-modality treatment, however, the results of the treatment will in many cases depend on the interactions between the various treatment modalities. This can be expressed as follows:

$$TE \neq \sum_{n=1}^{N} TE_n(p_n) \qquad \text{Equation 2}$$

$$SE \neq \sum_{n=1}^{N} SE_n(p_n) \qquad \text{Equation 3}$$

where the $p_n$ represents the vector of the treatment parameter values $p_i$, $TE_n$ represents the treatment effect, and $SE_n$ represents the side effect for treatment modality n. Hence, optimizing the various treatment modalities in isolation is, in general, unlikely to produce an optimal multi-modality treatment protocol.

In the case of a multi-modality treatment, the treatment 202 and side 204 effect may be expressed as follows:

$$TE = TE(p_1, p_2, \ldots p_n, p_{combi}) \qquad \text{Equation 4}$$

$$SE = SE(p_1, p_2, \ldots p_n, p_{combi}) \qquad \text{Equation 5}$$

where $p_{combi}$ is a vector of parameters that describes the interactions between the various treatment modalities, including for example the effects of the sequence and timing of the applied treatments.

In the case of a combination treatment, a goal of the treatment modeler 102 can be expressed as finding the vector of the treatment parameters $p_n$ for which $$\text{Delta}(p_n) \propto TE(p_1, p_2, \quad . \quad . \quad . \quad p_n, p_{combi}) - SE(p_1, p_2, \ldots p_n, p_{combi}) \qquad \text{Equation 6}$$

reaches a maximum or other desired value. Again, the optimization problem may be subject to various boundary conditions 119 and goals 106. Suitable optimization functions include but are not limited to known iterative, recursive, analytical, rule-based, and heuristic optimization functions and may be selected by those of ordinary skill in the art based on application-specific considerations.

The parameters that describe the interactions between the various treatment modalities are likewise application-specific. One suitable approach is the use of combination index (CI) analysis, which can be used to describe the synergistic or antagonistic effects of two or more treatments administered in conjunction. In a two treatment modality case in which the interaction is described as a function of dose, the CI can be expressed as follows:

$$CI = \frac{D_1}{D_{x1}} + \frac{D_2}{D_{x2}} + \frac{D_1 D_2}{D_{x1} D_{x2}} \qquad \text{Equation 7}$$

where $D_1$ and $D_2$ represent the doses applied using the first and second treatment modalities and $D_{x1}$ and $D_{x2}$ represent the doses required to provide a desired treatment effect (e.g., inhibiting the growth of x % of target cells) by means of the first or second treatment modality alone. If CI is less than 1, the treatments are synergistic; if CI is equal to one, the treatments are additive; if CI is greater than 1, the treatments are antagonistic. Note that Equation 7 applies to treatment modalities that have mutually non-exclusive mechanisms of action (e.g., those treatments that are non-competitive inhibitors of each other). Where the treatment modalities have the same or similar modes of action, the third term may be omitted. One tool for analyzing interactions in the pharmaceutical context is the known Calcusyn software package available from Biosoft of Cambridge, United Kingdom (biosoft.com).

A first example optimization task will now be described in the context of a treatment in medical oncology in which a first treatment modality includes a targeted internal radiation therapy (TRT) agent that is transported though the vasculature and the second treatment modality employs a perfusion modulating agent (PMA). The PMA modifies the perfusion of a tumor and thus influences the treatment effect of the TRT agent. For the purposes of the present example, it will be assumed that the PMA is to be applied prior to TRT agent, although an optimal sequence of application may also be considered if desired. The TCP and NTCP of the combined treatment can be calculated as follows:

$$TCP_{combi} = TCP(E_{PMA} + w_{TRT} * P * E_{TRT}) \qquad \text{Equation 8}$$

$$NTCP_{combi} = NTCP(w'_{TRT} * P * S_{TRT}) \qquad \text{Equation 9}$$

where
t Time interval between administration of PMA and TRT
$c_{PMA}$ Concentration of perfusion-modulating agent
$c_{TRT}$ Concentration of targeted radiotherapy agent
$w_{TRT}$ Dependence of TRT effect on perfusion, specific for each agent
$W'_{TRT}$ Dependence of TRT side effect on perfusion
$P = P(c_{PMA}, t)$ Relative Perfusion compared to un-modulated condition
$E_{PMA} = E(c_{PMA})$ Therapeutic effect of perfusion-mod. agent alone
$E_{TRT} = E(c_{TRT})$ Therapeutic effect of TRT alone on target tissue
$S_{TRT} = S(c_{TRT})$ Side effect of TRT alone on normal tissue
and $c_{PMA}$, $c_{TRT}$ and t represent the treatment variables to be optimized. By analogy to Equation 6, the treatment modeler 102 thus optimizes the function $$\text{Delta}(c_{PMA}, c_{TRT}, t) = \text{TCP}_{combi} - \text{NTCP}_{combi} \quad \text{Equation 10}$$

A second example optimization will now be described in the context of a treatment in medicine where the first treatment modality includes a radioimmunotherapy (RIT) agent that employs radiolabeled monoclonal antibodies (mAbs). The antibodies bind to target sites such as antigens present in the patient, hence applying a radiation dose in the vicinity of the binding site. The RIT agent is ordinarily introduced in the vasculature and distributes in the body over time.

The applied dose is limited by the detrimental side-effects of the treatment on risk organs and their functions. In the case of complete mAbs in cancer therapy, the primary risk organ is the bone marrow; for antibody fragments, the primary risk organs tend to be the kidney or liver. The dosage for the known agents Zevalin and Bexxar, for example, is limited by myelosuppression, which typically develops by week four to six and reaches a nadir by about week seven to nine. Thus, reducing myelosuppression would ordinarily permit the use of a relatively higher dose, leading to a higher therapeutic index. Viewed from another perspective, reducing myelosupression would be expected to reduce the side effects produced by a given dose.

Turning now to FIG. 3 the abscissa or x-axis depicts time and the ordinate or y-axis depicts concentration of the RIT agent. Curve 302 depicts the concentration at the tumor and curve 304 depicts the blood pool concentration, in each case for complete antibodies. The concentration at the tumor increases as the antibodies bind to antigens at the tumor site, approaching a limit value as the tumor site becomes saturated. The blood pool concentration, on the other hand, decreases as a function of time as the agent is cleared from the body. As indicated by an example time 306 following introduction of the agent, the concentration at the tumor has reached substantially its maximum value. The residual blood pool concentration, which contributes an undesirable dose burden to healthy tissues, nonetheless remains significant. Thus, in the present example, the second treatment modality includes the removal of unbound agent from the blood pool via a vascular filtering technique that will be described further below.

In general, the optimization goal is to define the parameters of a treatment protocol that reduces the unbound agent in the blood pool while still providing a sufficient concentration at the tumor site. The TCP and NTCP of the combined treatment can be calculated as follows:

$$\text{TCP}_{combi} = \text{TCP}[E_{TRT}(c'_{TRT,tumor}, A_{inj})] \quad \text{Equation 11}$$

$$\text{NTCP}_{combi} = \text{NTCP}\{S_{TRT}[c'_{TRT,blood}(t_1, E_{filt}, t_2), A_{inj}]\} \quad \text{Equation 12}$$

where
$t_1$(agent) Time interval between injection and start of filter procedure
$t_2$ Duration of filter procedure
$A_{inj}$ Injected therapeutic activity
$c'_{TRT,blood}$ = Concentration of agent in blood pool per injected activity
$c_{TRT,blood}/A_{inj}$
$c'_{TRT,tumor}$ = Concentration of agent at tumor site per injected activity;
$c_{TRT,tumor}/A_{inj}$ Assumption: unaffected by filtering due to specific and persistent binding
$S_{TRT} = S(c_{TRT})$ Side effect of TRT alone on normal tissue
$E_{TRT} = E(c_{TRT})$ Therapeutic effect of TRT alone on target tissue
$E_{filt}$ Efficiency of filter procedure
and $A_{inj}$, $t_1$, $t_2$, and possibly also $E_{filt}$ (if this can be affected by different filter settings) represent the treatment parameters to be optimized. Optimization is performed as described above in relation to Equation 10.

A third example will now be described in relation to a treatment regimen in which the treatment space 104 includes an IRT, an ERT, and a PMA. As the radiosensitization induced by the PMA is likely to depend on the dose rate of the applied radiotherapy, it is calculated separately for the ERT and IRT. As the dose rate of an applied IRT is typically lower than that of an applied ERT, the effect of the PMA on the received dose can be expected to be relatively greater for the IRT than the ERT.

For the purposes of the present example, the optimization goal is to define treatment parameters that maximize the dose that is effectively applied to the tumor while minimizing the dose that is effectively applied to risk organs. A suitable model can be expressed as follows:

$$d_t = d_{IRT,t}(p) + d_{ERT,t} \quad \text{Equation 13}$$

$$d_r = d_{IRT,r}(p) + d_{ERT,r} \quad \text{Equation 14}$$

$$p = p(PMA) \quad \text{Equation 15}$$

where
$d_t$ Dose received by the target
$d_r$ Dose received risk organs
$p(PMA)$ Effect of the radiosensitizer or PMA
$d_{IRT,t}$ IRT dose applied to the target
$d_{ERT,t}$ ERT dose applied to the target
$d_{IRT,r}$ IRT dose applied to the risk organs
$d_{ERT,r}$ ERT dose applied to the risk organs
and the IRT, ERT, and PMA doses are the treatment parameters to be optimized. Optimization is by analogy to Equation 10. Note that the effect of the PMA on target perfusion patterns can be extracted from the literature, determined via suitable experimental or analytical studies, or the like. Note that, while the above example has focused on a treatment regimen that includes an IRT, ERT, and a PMA, other treatment modalities are also contemplated. In one such example, the treatment regimen may include an TRT and/or an RIT, either supplementary to or supplanting the IRT.

More generally, other information can be used to estimate the effects of and/or improve the interaction of the treatment modalities. Again in the context of oncology, examples include hypoxia (obtained, for example, by FMISO-PET imaging techniques), findings from biopsy or histology, and the effect of bone marrow supporting agents (e.g., bone marrow stimulating or radioprotective agents). Likewise, the effect and/or synergistic potential of agents that modify rather than directly attack the target (e.g., anti-angiogenesis agents) may also be considered. Signal and effect chains within different cell types and the interaction with mechanical, radiation, thermal, chemical, or other agents may also be considered.

Note that the techniques described above, and particularly the functions performed by the treatment modeler 102 and the treatment modality filter 108, may be implemented by way of software, firmware, or other computer readable instructions stored on a computer readable medium. When executed by a computer, the instructions cause the computer to carry out the described techniques. The treatment modality models 112, goal state 106, and the modality treatment plans 128 may likewise be organized in suitable data structures and stored on a computer readable medium. It will also be appreciated that the computer and various media may be located at physically dispersed locations, with the instructions and/or data being transferred via the internet or other suitable communication networks.

Turning now to FIG. 4, a vascular filter arrangement 400 will now be described. The arrangement includes a pump 402 and filter 404 in fluid communication with the vasculature of a subject 406 via tubing or other suitable fluid connectors 408. As illustrated, the filter arrangement 400 forms a closed loop system in which blood is removed from the subject, filtered, and returned to the subject. Note that the filtering is typically performed in sterile setting.

With reference to FIG. 5, the filter 404 includes a housing 502 such as a conventional filtration column that includes an inlet 510 and an outlet 512, a carrier 504, and a filtration agent 506. The filtration agent 506 is selected for its ability to bind to or otherwise filter a material of interest, and the carrier 504 carries or otherwise supports the filtration agent 506 in the column 502.

In one implementation, the filtration agent 506 includes an antibody, glycoprotein, other protein, peptide, or other ligand that binds to a material of interest that is present in the object; example materials of interest include but are not limited to treatment agents that include antibodies, antibody fragments, peptides, or other materials having an affinity to a pathology of the patient.

In an application where a treatment agent employs antibodies 508, the carrier may include polystyrene beads having an enhanced surface area and a diameter in the range of about 30-60 micrometers (μm). One source of suitable beads includes polystyrene hydrazine beads available from Pierce Biotechnology of Rockford, Ill., U.S.A. (piercenet.com). The surface of the beads includes an antigen selected for its affinity to the antibodies of the treatment agent. In the case of Zevalin or Bexxar, for example, the ligand would include CD20 antigens. The column 502 is configured to permit a desired flow rate, for example on the order of about 500 milliliters (ml) per minute.

In operation, blood is removed from the patient and circulated through the filter. Unbound agent present in the blood binds to the antigen, thereby reducing the concentration of the agent. The treated blood is then returned to the patient. While the above description has focused on a closed-loop fluid flow system similar to that employed in techniques such as dialysis, batch or other similar filtering techniques may also be employed. Note also that the filtering may also be applied to bodily fluids other than blood.

An operation of the treatment planning system 100 will now be described in relation to FIG. 6.

A treatment effect is modeled at 602, for example by using a suitable mathematical model to predict the effects of a treatment protocol that includes one or more treatment modalities. Where the modeled treatment protocol employs a plurality of treatment modalities, a combined treatment effect of the various treatment modalities may be calculated, taking into account an interaction between two or more of the treatment modalities.

A side effect of the treatment is modeled at 604. Again, a combined side effect of the various treatment modalities may be modeled.

The side and treatment effects of the treatment are modeled at 606. As described above, for example, a difference between a treatment effect and a side effect may be calculated.

At 608, the effects of the modeled treatment are compared to a goal state.

If the modeled treatment does not satisfy the goal state, the modality filter parameters may be adjusted at 610. For example, an initial modeling operation may include a single treatment modality, while additional modeling operations may include different or additional treatment modalities. In one implementation, the modeling may be terminated when the modeled treatment satisfies the goal state. Where a goal is to produce an optimum treatment, other solutions may be considered until an optimum treatment is identified or the modeling is otherwise terminated.

At 610, a result of the modeling is used to generate the treatment protocol 610. Note that the treatment protocol may include only a contribution from a single modality. The generated treatment protocol may also be presented to a human user for review and/or acceptance, for example via a suitable computer monitor, printout, or other human interface.

The treatment protocol is applied at 612.

While the above description has focused on treatments involving oncology in medicine, it will be understood that the above-described techniques may be applied to other medical applications, as well as in industrial or other non-medical applications. For example, another medical application includes the treatment of acute or chronic inflammation.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A non-transitory computer readable storage medium containing instructions which, when executed by a computer, cause the computer to carry out a method comprising:
   modeling a treatment effect of a first treatment modality, wherein the treatment effect of the first treatment modality includes a dose of the first treatment modality applied to a first target portion of an object;
   modeling a side effect of the first treatment modality, wherein the side effect of the first treatment modality includes a dose of the first treatment modality applied to a first non-target portion of the object;
   modeling a treatment effect of a second treatment modality, wherein the treatment effect of the second treatment modality includes a dose of the second treatment modality applied to a second target portion of the object;
   modeling a side effect of the second treatment modality, wherein the side effect of the second treatment modality includes a dose of the second treatment modality applied to a second non-target portion of the object;

modeling a combined treatment effect (TE) of the first and second treatment modalities, including an interaction between the first and second treatment modalities;

modeling a combined side effect (SE) of the first and second treatment modality, including an effect of an interaction between the first and second treatment modality; and using a result of the modeling of the combined treatment effect of the first and second treatment modalities and of the combined side effect of the first and second treatment modalities to generate a treatment protocol having treatment parameters of the first and second treatment modalities for application to the object, wherein the treatment protocol is implemented to apply the first and second treatment modalities to the object based on the treatment parameters of the treatment protocol.

2. The computer readable storage medium of claim 1 wherein the method includes seeking a treatment protocol that satisfies a goal state.

3. The computer readable storage medium of claim 2 wherein the goal state includes first and second goals and the method includes determining a figure of merit that weights first and second effects of a treatment.

4. The computer readable storage medium of claim 1 wherein the method includes calculating, for a vector of treatment parameters $p_n$:

Delta$(p_n) \propto$ TE$(p_1, p_2, \ldots p_n, p_{combi})$−SE$(p_1, p_2, \ldots p_n, p_{combi})$, wherein delta$(p_n)$ is a therapeutic gap between the combined treatment effect and combined side effect.

5. The computer readable storage medium of claim 1 wherein the method includes finding a vector of treatment parameters for which Delta$(p_n)$ has a maximum value.

6. The computer readable storage medium of claim 1 wherein the method includes determining a sequence in which the first and second treatment modalities should be applied to the object.

7. The computer readable storage medium of claim 1 wherein the method includes predicting a treatment effect of a treatment protocol that includes the first and second treatment modalities, wherein the prediction includes an effect of an interaction between the first and second treatment protocols.

8. The computer readable storage medium of claim 1 wherein the treatment effect includes a tumor control probability.

9. The computer readable storage medium of claim 1 wherein the first treatment modality includes a treatment agent that includes a material that binds to a target of the object and the second treatment modality includes a filter including a ligand that binds to the material.

10. The computer readable storage medium of claim 1 wherein the first treatment modality includes the application of radiation at a first rate, the second treatment modality includes a perfusion modulating agent or a radiosensitizer, and using a mathematical model includes modeling a treatment effect of a third treatment modality that includes the application of radiation at a second rate, wherein the first rate is less than the second rate.

11. The computer readable storage medium of claim 2 wherein modeling includes modeling an effect of the first treatment modality as a function of information from an imaging examination of the object or object demographic information.

12. The computer readable storage medium of claim 2 wherein modeling includes employing an adaptive treatment model to model an effect of the first treatment modality.

13. A method comprising:

using a mathematical model to model a treatment effect of a first treatment modality wherein the treatment effect of the first treatment modality includes a dose of the first treatment modality applied to a first target portion of an object;

using a mathematical model to model a side effect of the first treatment modality, wherein the side effect of the first treatment modality includes a dose of the first treatment modality applied to a first non-target portion of the object;

using a mathematical model to model a treatment effect of a second treatment modality, wherein the treatment effect of the second treatment modality includes a dose of the second treatment modality applied to a second target portion of the object;

using a mathematical model to model a side effect of the second treatment modality, wherein the side effect of the second treatment modality includes a dose of the second treatment modality applied to a second non-target portion of the object;

using a mathematical model to model a combined treatment effect of the first and second treatment modalities, including an interaction between the first and second treatment modality;

using a mathematical model to model a combined side effect of the first and second treatment modalities, including an interaction between the first and second treatment modality; and using a result of the modeling of the combined treatment effect of the first and second treatment modalities and of the combined side effect of the first and second treatment modalities to generate a treatment protocol for application to the object, wherein the treatment protocol includes treatment parameters of the first and second treatment modalities; and implementing the treatment protocol to apply the first and second treatment modalities to the object based on the treatment parameters of the treatment protocol.

14. The method of claim 13 wherein the side effect includes a normal tissue complication probability.

15. The method of claim 13 wherein the first treatment modality includes an external radiation therapy and the second treatment modality includes an internal radiation therapy.

16. The method of claim 13 wherein the treatment protocol includes a temporal duration between an application of the first treatment modality and an application of the second treatment modality.

17. The method of claim 13 wherein the first treatment modality includes the application of a first agent that produces a treatment effect and a side effect, the second treatment modality removes the agent from the subject so as to mitigate the side effect, and the interaction includes an effect of the removal of the second agent on the side effect.

18. The method of claim 13 wherein the model includes an observed response of the object to an applied treatment.

19. The method of claim 13 including:

using a result of the modeling to generate first and second suggested examination protocols;

presenting the suggested examination protocols to a human user;

receiving a response of the user.

20. The method of claim 13, wherein the method includes calculating, for a vector of treatment parameters $p_n$:

$\text{Delta}(p_n) \propto \text{TE}(p_1, p_2, \ldots p_n, p_{combi}) - \text{SE}(p_1, p_2, \ldots p_n, p_{combi})$, wherein $\text{delta}(p_n)$ is a therapeutic gap between the combined treatment effect and combined side effect.

* * * * *